United States Patent
Redel et al.

(10) Patent No.: US 7,729,746 B2
(45) Date of Patent: Jun. 1, 2010

(54) THREE-DIMENSIONAL CO-REGISTRATION BETWEEN INTRAVASCULAR AND ANGIOGRAPHIC DATA

(75) Inventors: Thomas Redel, Poxdorf (DE); Estelle Camus, Erlangen (DE); Oliver Meissner, München (DE)

(73) Assignee: Siemens Aktiengesellschaft, Munich (DE)

( * ) Notice: Subject to any disclaimer, the term of this patent is extended or adjusted under 35 U.S.C. 154(b) by 1244 days.

(21) Appl. No.: 11/266,886

(22) Filed: Nov. 4, 2005

(65) Prior Publication Data

US 2007/0123771 A1    May 31, 2007

(51) Int. Cl.
*A61B 5/05* (2006.01)
(52) U.S. Cl. .................. 600/428; 600/427; 600/431; 600/433
(58) Field of Classification Search .................. 600/427, 600/428, 431, 433
See application file for complete search history.

(56) References Cited

U.S. PATENT DOCUMENTS 6,148,095 A * 11/2000 Prause et al. ................ 382/131

OTHER PUBLICATIONS

Dagres et al, "The Echo Map System: Online Integration of Intracoronary Ultrasound and Doppler Images into Angiographic Images During Cardiac Catheterization. Influence on Radiation Exposure and Procedure Parameters", Journal of Interventional Cardiology, vol. 17, No. 5, 2004, pp. 321-325.

* cited by examiner

*Primary Examiner*—Brian Casler
*Assistant Examiner*—John F Ramirez
(74) *Attorney, Agent, or Firm*—Schiff Hardin LLP

(57) ABSTRACT

A method and appertaining system permit a co-registration between points in a three-dimensional model of a vessel and vascular images obtained by an imaging catheter within the vessel at the respective points. The three-dimensional model is created by utilizing information from at least two external two-dimensional images produced by, e.g., one or more x-ray devices. The three-dimensional model is displayed on an analysis workstation, and a user may view the vascular images at particular points by selecting the appertaining points on the three-dimensional model.

15 Claims, 3 Drawing Sheets

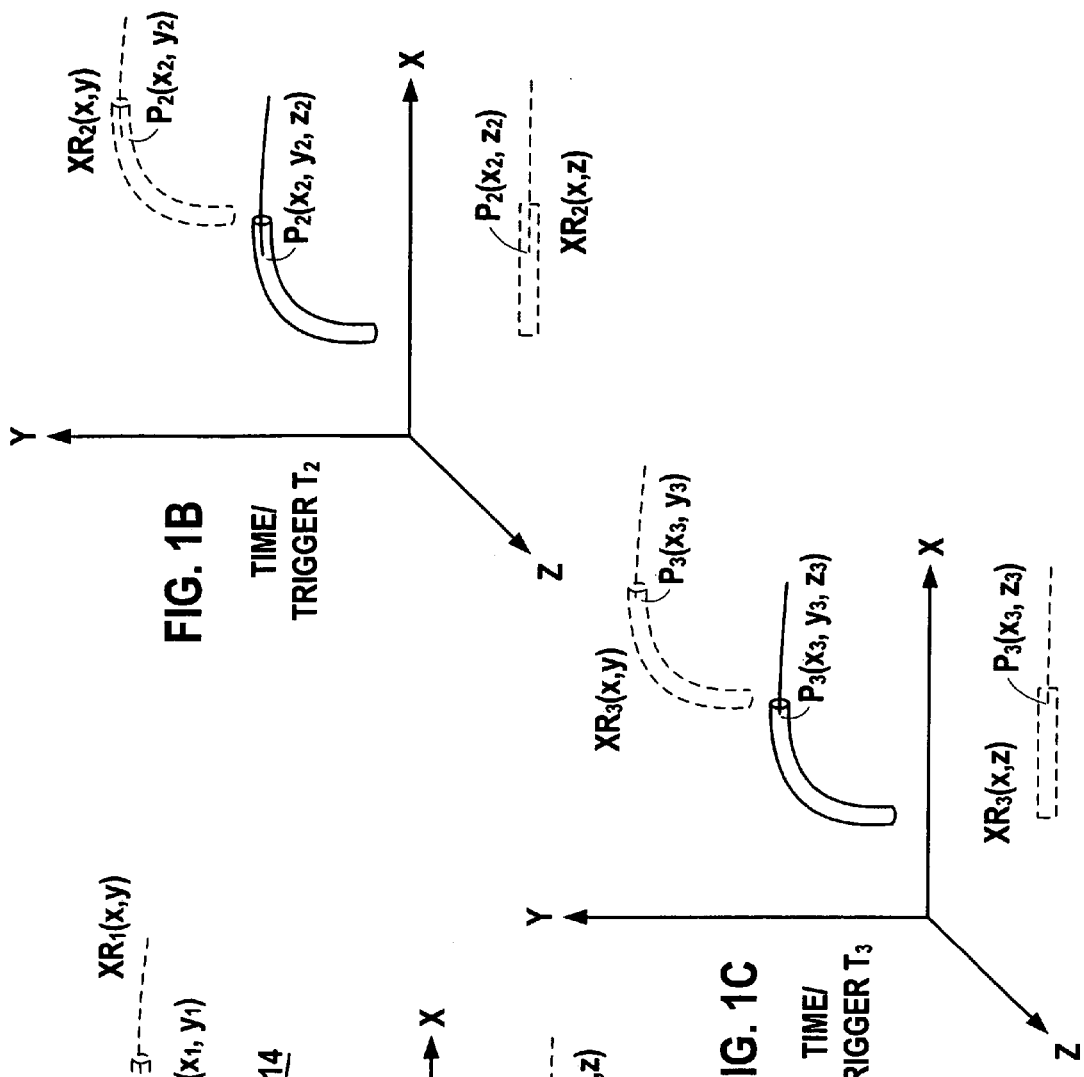

$T_3, P_3(x_3, y_3, z_3)$ $T_2, P_2(x_2, y_2, z_2)$ $T_1, P_1(x_1, y_1, z_1)$

THREE-DIMENSIONAL CO-REGISTRATION BETWEEN INTRAVASCULAR AND ANGIOGRAPHIC DATA

BACKGROUND

The invention relates to the field of providing a three-dimensional co-registration between intravascular and angiographic data.

For quantification of the build-up of atherosclerotic plaques in blood vessels and therapy planning, x-ray projections are acquired with injection of contrast agent into the appertaining vessel in a catheter laboratory and analyzed two-dimensionally or possibly three-dimensionally. In some cases, an intravascular imaging (for example, optical coherence tomography (OCT) or intravascular ultrasound (IVUS)) is also referenced in order to obtain further information about the morphology and other properties of the plaque.

When OCT or IVUS images are acquired using the "pull-back" method, x-ray projections are also simultaneously acquired in order to check the position of the tip of the OCT or IVUS catheter in real time. The problem is that, in this method, the images are stored on separate platforms such that afterwards a temporal association/registration is no longer possible. Given a review of the images, the user is therewith no longer in the position to recognize which OCT or IVUS image shows which point in the vessel.

In practice, doctors look for anatomical landmarks (for example, bifurcations or a number of side branches) that can be recognized both on the x-ray projections and on the intravascular images and thus orient themselves in the vessel. However, this is a very involved, time-consuming, and imprecise method.

A solution to this problem is disclosed in Dagres, Haude Kurreck, Bamugart and Erbel, "The EchoMap system: online integration of intracoronary ultrasound and procedure parameters", Journal of Interventional Cardiology, Vol. 17, No. 5, 2004, that goes by the name of EchoMap in connection with an IVUS apparatus. EchoMap offers a picture-in-picture representation of IVUS images and x-ray projections during an IVUS withdrawal. After the pullback, the complete scene of the picture-in-picture scene can be stored. The disadvantage of this method is that the IVUS images or x-ray projections cannot be processed in the picture-in-picture representation. Moreover, a region of the x-ray projections is not visible (since it is covered with the IVUS image) and the IVUS images are shown very small.

SUMMARY

In the present invention, a method is described in which the doctor can examine vessels with an intravascular imaging modality (such as OCT or IVUS) and simultaneously with x-ray projections for monitoring of the pullback, whereby all invasively-acquired images are registered online with an existing 3D reconstruction of the x-ray projections and are also shown again together after the pullback.

Accordingly, a method is provided for co-registering vascular images with a 3D reconstruction of a vessel, comprising: triggering a first 2D external angiographic image in a first imaging plane; triggering a second 2D external angiographic image in a second imaging plane; reconstructing a 3D model image from the first 2D external angiographic image and the second 2D external angiographic image; inserting a catheter with an imaging device at its tip into the vessel to a starting point; triggering a first 2D external image that shows a tip location at the starting point in two dimensions in a first imaging plane without contrast agent injection; triggering a second 2D external image that shows the tip location at the starting point in two dimensions in a second imaging plane without contrast agent injection; reconstructing the starting point of the tip location in three dimensions from the first 2D external image and the second 2D external image and visualization in the previously obtained 3D model; starting a pull-back of the catheter and simultaneously acquiring vascular images until an endpoint of the pull-back is reached; defining a passed route of the catheter tip based on at least one of: a) a pullback speed and elapsed time; and b) an image rate and a sequential image number in the 3D model; co-registering the vascular images with the route of the catheter tip in the 3D model; displaying the 3D model image on a display with a marker representing the position of the vascular image with respect to the position of the catheter tip along the route; displaying the vascular image co-registrated with the visualized marker.

Correspondingly, a system is provided for co-registering vascular images with a 3D reconstruction of a vessel, comprising: a catheter having an imaging device at its tip; a catheter image processor that receives a first vascular image from the catheter imaging device when the catheter is at a starting point, receives a second vascular image from the catheter imaging device when the catheter is at a second point and stores the images in a storage device; a 2D external angiographic imaging device that captures a first 2D external angiographic image in a first imaging plane that shows a catheter tip location when the catheter tip is at the starting point within the vessel and that captures a third 2D external angiographic image in a first imaging plane that shows a catheter tip location when the catheter tip is at the second point within the vessel; at least one of: a) an additional 2D external angiographic imaging device that captures, and b) the 2D external angiographic imaging device capturing, a second 2D external angiographic image in a second imaging plane that shows a catheter tip location when the catheter tip is in the starting point within the vessel and a fourth 2D external angiographic image in a second imaging plane that shows a catheter tip location when the catheter tip is in the second point within the vessel; a 3D reconstructor that produces a 3D model image that includes the tip location at the starting point in three dimensions from the first 2D external angiographic image and the second 2D external angiographic image and that includes the tip location at the second point in three dimensions from the third 2D external angiographic image and the fourth 2D external angiographic image, and stores the 3D model image in the storage device; an analysis workstation comprising: a co-registration program that associates the first vascular image with the starting point in three dimensions, and associates the second vascular image with the second point in three dimensions; a display that displays the 3D model image in a first region of the display; and a selection device that is used to select one of the points in three dimensions from the 3D model image and causes the display to display the associated vascular image in a second region of the display.

An exemplary embodiment with application in cardiology (with respect to cardiac vessels) is described in the following. However, this method can also be applied in other regions, for example, in abdominal angiography and in neurology; ECG triggering or acquisition of ECG signals is thereby not absolutely necessary. The application to bifurcations of vessels is naturally also conceivable with the invention. Both separate modalities and integrated modalities can be used according to the invention.

Many advantages may be provided with the invention, including: a) the time gained in the pullback monitoring and in the review of the acquired images, b) the concise representation provided during the pullback and in the review of the images, c) a simple operation of the intravascular modality during the pullback, and d) the provision of 3D information about the vessel state that are registered and displayed together. This can further result in a possible saving of the dose of online irradiation during monitoring of the pullback.

DESCRIPTION OF THE DRAWINGS

The invention is described below with reference to a preferred embodiment that is illustrated in the following drawings.

FIGS. 1A-C are pictorial diagrams illustrating a vessel with the an inserted catheter positioned a different points of time during the imaging;

DETAILED DESCRIPTION OF THE PREFERRED EMBODIMENTS

Figure 2C:
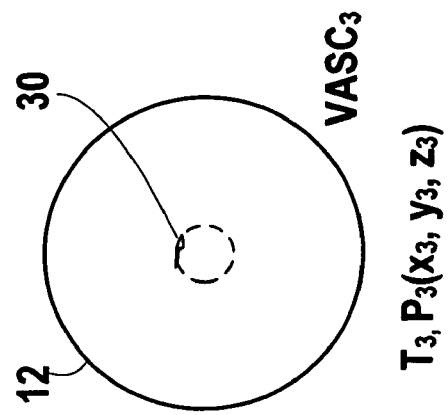
FIGS. 2A-C are pictorial illustrations of the vessel imaging taken at the points of time illustrated in FIGS. 1A-C.
Figure 2B:
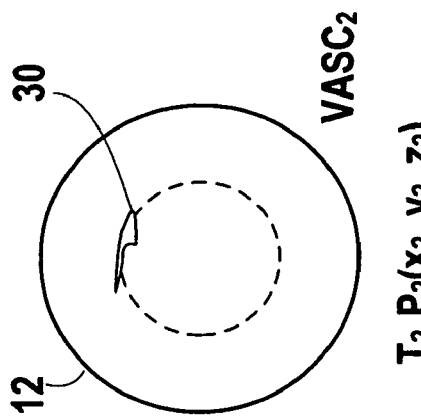
Figure 2A:
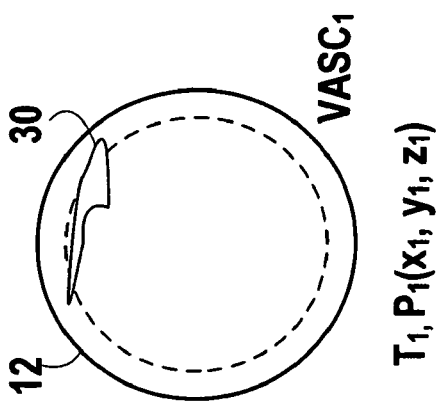

According to a preferred embodiment of the invention discussed below, a method is provided in which an x-ray system is adjusted for the examination procedure, such as providing a proper angle for the C-arm, position of the patient table, etc. FIGS. 1A-C illustrate a vessel 12 of a subject. The subject is injected with a contrast agent, and x-ray projections XR are acquired with an ECG triggering of the cardiac vessel to be examined in at least two viewing angles (optimally 90° from one another—shown are x,y and x,z planes), i.e., either in the biplanar mode or two successive exposures or rotation angiography. Regarding the use of x-ray projections, the x-ray projections XR are acquired with contrast agent injection in order to conduct a 3D reconstruction VOL (FIG. 3) of the geometry of the vessel 12 or of the lesion 30 to be examined. The x-ray projections XY are acquired without contrast agent injection in order monitor the progress of the pullback. During the pullback, a monoplanar acquisition is sufficient; however a biplanar acquisition also possible. The position of the patient table may thereby not change.

A 3D reconstruction VOL of the cardiac vessel 12 can be created using the at least two x-ray projections XR described above using, for example, the interventional cardiac 3D (IC3D) method, which allows a 3D volume VOL image to be created based on two or more different projections XR(x,y), XR(x,z) such that the 3D image VOL can be visualized from any chosen angle. Optionally, various parameters of the vessel 12 may be quantified in the 3D representation VOL.

The procedure then involves determining, by the doctor, the start point $P_1(x_1,y_1,z_1)$ of the pullback of the intravascular modality at time or trigger $T_1$ and then acquiring two x-ray projections (optimally positioned with respect to one another by approximately 90°) $XR_1(x,y)$, $XR_1(x,z)$ in which the catheter tip 16 is visible. Using the pullback method and by acquiring the intravascular images VASC, the pullback speed thereby monitored and simultaneously the ECG signal or ECG triggering 130 (FIG. 3) for ECG registration is acquired with the 3D reconstruction. FIGS. 1A-C and 2A-C illustrate the starting point $P_1$ and two subsequent stages during the pullback $P_2$, $P_3$. Optionally during the pullback, x-ray projections XR (without contrast agent injection) may be simultaneously acquired in which the tip 16 of the intravascular catheter 14 is visible (for monitoring of the pullback).

During the pullback, the system creates a representation of the 3D reconstruction VOL (acquired in the previously described step) of the vessel 12 and of a marker 16 whose position in the 3D lumen 12 corresponds to the position of the tip 16 of the intravascular catheter 14 in quasi-real time. The co-registration begins with the registration of the start point $P_1$ of the pullback. Registration of the catheter tip 16 at the start point $P_1$ of the pullback is indicated with a marker 16 in the 3D reconstruction VOL of the vessel 12. The two x-ray projections $XR_1(x,y)$, $XR_1(x,z)$ are acquired (without a contrast agent injection) at approximately 90° from one another at the start point $P_1(x_1,y_1,z_1)$ of the pullback, in which x-ray projections the catheter tip 16 is visible, and are registered with the 3D representation $VOL_1(x,y,z)$ using the C-arm setting (the position and angulation). The catheter tip 16 is automatically detected on these x-ray projections $XR_1$ with a computer program or is provided by the user (by selecting, with e.g., a mouse 160 click, on the x-ray projection $XR_1$); its position in the 3D space $P_1(x_1,y_1,z_1)$ is detected and indicated in the 3D representation $VOL_1$ of the vessel 12 (in the vessel lumen).

Co-registration continues as the pullback continues (time/ trigger points $T_2$, $T_3$). When the position of the start point $P_1(x_1,y_1,z_1)$ of the pullback is known in the 3D representation VOL, the further positions $P_2(x_2,y_2,z_2)$, $P_3(x_3,y_3,z_3)$ of the catheter tip 16 can be derived using the passed route of the catheter tip 16 relative to the start point $P_1(x_1,y_1,z_1)$. This route may be provided by the pullback speed (mm/s) and the elapsed time or image rate (images/s) and image number. With the assumption that the catheter tip 16 is always located on the center line of the vessel lumen 12 or via the application of a centering catheter device 14, the catheter position P is indicated in quasi-real time ("quasi" implying after calculation of the passed route) in the 3D representation VOL by a marker on the center line of the vessel lumen 12. EKG-synchronous image data/information may be utilized.

Figure 3:
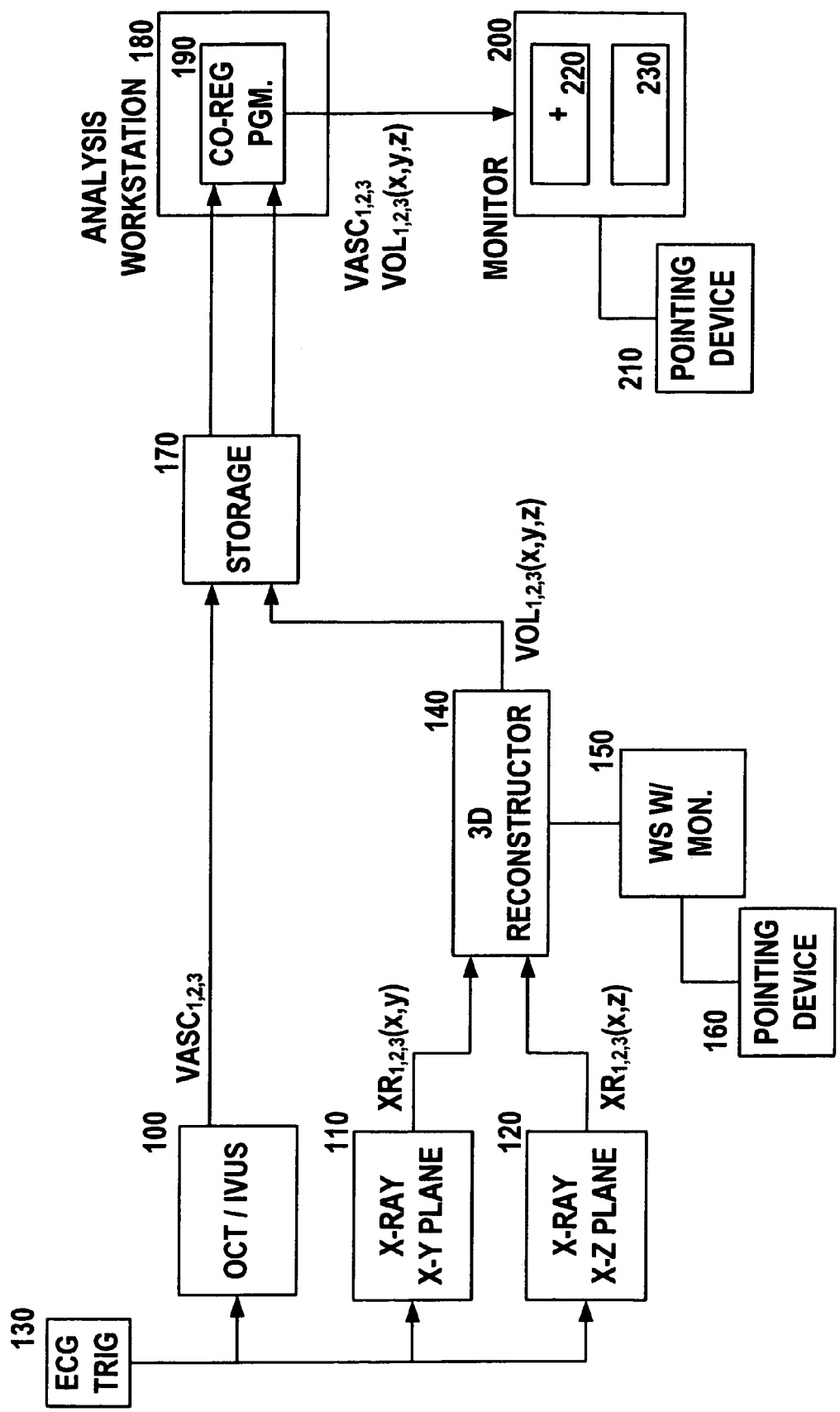
FIG. 3 is a block diagram of the system.

Referring to FIG. 3, the 3D reconstruction VOL is created by a 3D reconstructor 140 from the two X-rays XR(x,y), XR(x,z) of the two orthogonal X-ray imagings 110, 120 created from the EKG-registered intravascular VASC (100) and x-ray images XR may then be archived in an image store 170 and/or transmitted to a workstation 180 for further analysis, review, and/or processing. The imagings 110, 120 may be generated by a single imaging device or by two imaging devices. A co-registration program 190 may then be utilized on the workstation 180 to review the images VASC, VOL. When a user with a pointing device 210 selects or clicks a location in the vessel on the 3D reconstruction 220 of the vessel displayed on the monitor 200, the corresponding intravascular image VASC is automatically, additionally displayed 230. The user can thus scroll through the entire vessel image 220 and the corresponding intravascular image 230 is automatically displayed.

Regarding the intravascular image data set $VASC_{1,2,3}$ that is, for example, acquired with an IVUS or with an OCT catheter 14, 100, the pullback method consists of initially positioning the catheter tip 16 distal from the lesion 30 in the vessel 12 and then drawing the catheter back with a controlled speed, both proximal to and through the lesion 30. The catheter tip 16 simultaneously acquires intravascular images VASC or information of the vessel 12 and displays these to the user. This method serves to provide to the doctor morphological information about the lesion 30 and the vessel wall that is complementary to the information about the anatomy acquired from the x-ray projections XR.

Other catheter-based invasive methods in which a pullback occurs (such as optical coherence tomography (OCT), optical frequency domain imaging (OFDI), intracardiac echocardiography (ICE), pressure wire, angioscopy, near-infrared fluorescence (NIRF) imaging, molecular imaging, intravascular magnetic resonance (MR) and other optical based cross sectional imaging techniques can also be used and co-registered.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method for co-registering vascular images with a 3D reconstruction of a vessel, comprising the steps of:
    triggering a first 2D external angiographic image in a first imaging plane;
    triggering a second 2D external angiographic image in a second imaging plane;
    reconstructing a 3D model image from the first 2D external angiographic image and the second 2D external angiographic image;
    inserting a catheter with an imaging device at its tip into the vessel to a starting point;
    triggering a first 2D external image that shows a tip location at the starting point in two dimensions in a first imaging plane without contrast agent injection;
    triggering a second 2D external image that shows the tip location at the starting point in two dimensions in a second imaging plane without contrast agent injection;
    reconstructing the starting point of the tip location in three dimensions from the first 2D external image and the second 2D external image and visualization in the previously obtained 3D model;
    starting a pull-back of the catheter and simultaneously acquiring vascular images until an endpoint of the pull-back is reached;
    defining a passed route of the catheter tip based on at least one of: a) a pullback speed and elapsed time; and b) an image rate and a sequential image number in the 3D model
    co-registering the vascular images with the route of the catheter tip in the 3D model;
    displaying the 3D model image on a display with a marker representing the position of the vascular image with respect to the position of the catheter tip along the route;
    displaying the vascular image co-registrated with the visualized marker.

2. The method according to claim 1, further comprising the step of:
    performing an online co-registration of the vascular images with the 3D model and online display of the 3D model image with a marker representing the position of the vascular image with respect to the position of the catheter tip along the route.

3. The method according to claim 1, wherein the triggering of the first 2D external angiographic image and the second angiographic 2D external image occur simultaneously with two separate 2D external imaging machines.

4. The method according to claim 1, wherein the first imaging plane and the second imaging plane are orthogonal.

5. The method according to claim 1, further comprising the steps of:
    utilizing an ECG triggering for the triggering of the 2D external images.

6. The method according to claim 1, wherein the reconstruction of the 3D model image comprises utilizing an interventional cardiac 3D method.

7. The method according to claim 1, further comprising:
    monitoring a pullback speed and ECG signal or ECG triggering for ECG registration for the 3D reconstruction.

8. The method according to claim 7, further comprising:
    utilizing a centering catheter device to ensure the centering of the catheter tip in the lumen.

9. The method according to claim 1, wherein for the co-registration only the vascular images are selected which are in or nearest to a same phase of a cardiac cycle as the one used for the reconstruction of the 3D model.

10. The method according to claim 1, wherein selecting the first and second points on the displayed 3D model image is done with a mouse and pointer on a display screen of the analysis workstation.

11. The method according to claim 1, further comprising:
    defining a passed route of the catheter tip based on at least one of: a) a pullback speed and elapsed time; and b) an image rate and a sequential image number.

12. The method according to claim 1, further comprising:
    performing the 2D external imaging with an x-ray machine.

13. The method according to claim 1, further comprising:
    performing the 2D vascular imaging with a method selected from the group consisting of optical coherence tomography (OCT), optical frequency domain imaging (OFDI), intracardiac echocardiography (ICE), pressure wire, angioscopy, near-infrared fluorescence (NIRF) imaging, molecular imaging, and intravascular magnetic resonance (MR) imaging or other optical based cross sectional imaging technique.

14. A method for co-registering vascular images with a 3D reconstruction of a vessel, comprising the steps of:
- triggering a first 2D external angiographic image in a first imaging plane;
- triggering a second 2D external angiographic image in a second imaging plane;
- reconstructing a 3D model image from the first 2D external angiographic image and the second 2D external angiographic image;
- inserting a catheter with an imaging device at its tip into the vessel to a starting point;
- triggering a first 2D external image that shows a tip location at the starting point in two dimensions in a first imaging plane without contrast agent injection;
- triggering a second 2D external image that shows the tip location at the starting point in two dimensions in a second imaging plane without contrast agent injection;
- reconstructing the starting point of the tip location in three dimensions from the first 2D external image and the second 2D external image and visualization in the previously obtained 3D model;
- starting a pull-back of the catheter and simultaneously acquiring vascular images until an endpoint of the pull-back is reached;
- defining a passed route of the catheter tip based on at least one of: a) a pullback speed and elapsed time; and b) an image rate and a sequential image number in the 3D model
- co-registering the vascular images with the route of the catheter tip in the 3D model;
- displaying the 3D model image on a display with a marker representing the position of the vascular image with respect to the position of the catheter tip along the route;
- displaying the vascular image co-registrated with the visualized marker;
- wherein the triggering of the first 2D external image and the second 2D external image occur simultaneously with two separate 2D external imaging machines.

15. A system for co-registering vascular images with a 3D reconstruction of a vessel, comprising:
- a catheter having an imaging device at its tip;
- a catheter image processor that receives a first vascular image from the catheter imaging device when the catheter is at a starting point, receives a second vascular image from the catheter imaging device when the catheter is at a second point and stores the images in a storage device;
- a 2D external angiographic imaging device that captures a first 2D external angiographic image in a first imaging plane that shows a catheter tip location when the catheter tip is at the starting point within the vessel and that captures a third 2D external angiographic image in a first imaging plane that shows a catheter tip location when the catheter tip is at the second point within the vessel;
- at least one of: a) an additional 2D external angiographic imaging device that captures, and b) the 2D external angiographic imaging device capturing, a second 2D external angiographic image in a second imaging plane that shows a catheter tip location when the catheter tip is in the starting point within the vessel and a fourth 2D external angiographic image in a second imaging plane that shows a catheter tip location when the catheter tip is in the second point within the vessel;
- a 3D reconstructor that produces a 3D model image that includes the tip location at the starting point in three dimensions from the first 2D external angiographic image and the second 2D external angiographic image and that includes the tip location at the second point in three dimensions from the third 2D external angiographic image and the fourth 2D external angiographic image which are obtained without contrast, and stores the 3D model image in the storage device;
- an analysis workstation comprising:
- a co-registration program that associates the first vascular image with the starting point in three dimensions, and associates the second vascular image with the second point in three dimensions;
- a display that displays the 3D model image in a first region of the display; and
- a selection device that is used to select one of the points in three dimensions from the 3D model image and causes the display to display the associated vascular image in a second region of the display.

* * * * *